United States Patent [19]

Dutton

[11] Plant 4,826

[45] Feb. 23, 1982

[54] POMEGRANATE TREE

[76] Inventor: James M. Dutton, 1043 Highland Ave., Visalia, Calif. 93277

[21] Appl. No.: 91,335

[22] Filed: Nov. 5, 1979

[51] Int. Cl.[3] ..... A01H 5/00
[52] U.S. Cl. ..... Plt./33
[58] Field of Search ..... Plt./33

[56] References Cited

U.S. PATENT DOCUMENTS

P.P. 3,520 3/1974 Wileman ..... Plt./33

*Primary Examiner*—James R. Feyrer
*Attorney, Agent, or Firm*—Huebner & Worrel

[57] ABSTRACT

A pomegranate tree generally similar to the Wonderful pomegranate tree (unpatented), but distinguished therefrom by bearing fruit which is more highly colored and ripens from seven to ten days earlier and further characterized by bearing fruit which is of a higher acid content when ripe than the fruit of the Granada pomegranate tree (U.S. Plant Pat. No. 2,618) or the Early Red (U.S. Plant Pat. No. 2,723), varieties which the subject variety most nearly resembles in appearance.

1 Drawing Figure

BACKGROUND OF THE NEW VARIETY

The present invention relates to a new and distinct variety of pomegranate tree generally similar to the "Wonderful" variety pomegranate tree (unpatented) of which it is a sport, but which bears fruit which ripens seven to ten days earlier and has a more highly colored rind and arils than the Wonderful, much in the manner of the Granada (U.S. Plant Pat. No. 2,618), which ripens approximately three weeks earlier than the subject variety and the Early Red (U.S. Plant Pat. No. 2,723) which ripens approximately two weeks earlier than the subject variety and from each of which the subject variety is distinguished by a much higher acid content and pungent flavor at maturity.

It is well known that the sales appeal of pomegranates is greatly influenced by size and exterior color of the fruit. When a pomegranate is eaten, the color of the edible arils, or seed coating of the variety, is an element in consumer satisfaction as is, of course, the acid content and flavor of the arils. As with other fruits, it is commercially desirable that a pomegranate tree bear fruit which ripens at a time when other fruits of that type are not available.

In pomegranates, the flavor is directly related to the acid content when fully ripe. However, it should be noted that the marketing regulations in effect in the State of California require that pomegranates not be marketed until the acid content of the arils established by titration is 1.85 percent or less.

The well-known Wonderful pomegranate tree (unpatented) produces fruit which is of relatively large size and has an acid content close to the maximum permitted under the California regulations when ripe. However, the exterior of the rind of pomegranates borne by this variety is frequently of a Pink (1 A 9) color rather than a Red (4 L 1) or "Old Red" (5 K 6) color desired in pomegranates for decorative purposes. When a fruit of this variety is opened, a susbstantial number of the arils are usually found to be colorless rather than to be of the strong red or moderate red desired red color.

The color deficiencies of the Wonderful variety of pomegranate tree have been overcome in other pomegranate tree varieties derived from the Wonderful variety, such as the Early Red variety (U.S. Plant Pat. No. 2,723) and the Granada variety of pomegranate (U.S.

Plant Pat. No. 2,618). These varieties also have the desirable characteristic of bearing fruit which ripens earlier than that of the Wonderful variety, the Early Red being three weeks earlier and the Granada four weeks earlier. At maturity, the acid content of the Granada variety is from 1.4 to 1.6 percent and that of the Early Red variety is from 0.7 to 1.4 percent. At maturity, both the Wonderful and the instant variety closely approach 1.85 percent.

It has been long recognized as desirable to provide a pomegranate which would bear fruit having a more highly colored rind and arils than that of the Wonderful variety, but which is of large size, superior flavor, and highly colored. It is especially desirable for the fruit of the subject pomegranate tree to ripen in the interval between the ripening of the above-identified early ripening varieties and the Wonderful variety so that a higher price can be obtained due to the lack of competition in the marketplace.

ORIGIN AND ASEXUAL REPRODUCTION OF THE NEW VARIETY

The new variety of pomegranate was discovered by me on Sept. 1, 1976, as a single mature tree growing in an orchard of Wonderful pomegranate trees (unpatented). The orchard is owned by me and is located on Avenue 208 on the west side of Highway 65 near the city of Lindsay, in the County of Tulare, in the state of California. The orchard was planted by my grandfather in 1921 or 1922 and the sport was not recognized as such until discovered in 1976 as a tree in the designated orchard.

The new variety of pomegranate tree was asexually reproduced under my supervision by rooting hardwood cuttings from said tree, and the fruit and tree characteristics resulting from the cuttings proved identical to those of the original tree.

SUMMARY OF THE NEW VARIETY

The instant variety of pomegranate tree is characterized by having the general tree characteristics of the Wonderful variety of which it is a sport, but has the important distinctions of bearing fruit which is more highly colored in rind and arils and which ripens from seven to ten days earlier. The rind of a pomegranate borne by the new variety has an exterior background color ranging from "Candy Pink" (2 H 10) to "Afghan" (5 L 6) with the lighter portion of the background having spots of "Afghan" and the arils attain a color from "Cherry Blossom" (4 J 4) to "Oxheart" (6 L 5). The instant variety bears fruit whose arils are more acid than the earlier varieties to which reference has been made. Thus, the flavor is more pungent. Under similar growing conditions, the pomegranates borne by the new variety are slightly smaller than those borne by the Wonderful variety.

The subject variety of pomegranate tree is distinguished from the Early Wonderful pomegranate tree (U.S. Plant Pat. No. 3,520) by the following characteristics:

1. The axillary angle, the angle between the stems and branches of twigs.

In the subject variety, this angle averages 59.2° while this angle averages 55.7° in the Early Wonderful variety. These angles were obtained by averaging twenty-five specimens of each variety, the standard deviation in the case of the subject variety being 6.5° and in the Early Wonderful variety being 8.5°, thereby distinguishing these two varieties as determined by well-known statistical methods.

2. The order of bud break, the breaking of dormancy in late winter or early spring of the two varieties.

The subject variety breaks four to five days before the well-known Wonderful variety (unpatented) whereas the Early Wonderful variety breaks from four to five days after the Wonderful variety and, therefore, eight to ten days after the subject variety.

3. The earlier leaf development of the subject variety.

On Mar. 5, 1980 trees of the subject variety were budded out and had leaflets measuring a centimeter or so in length while buds of the Early Wonderful variety, grown under as nearly identical environmental conditions as possible, were dormant, showed no swelling, and no leaves had appeared.

4. The later blooming period and somewhat later ripening of fruit of the subject variety.

The subject variety blooms from mid-April to July 1 while the Early Wonderful variety blooms from March 22, with full bloom being reached by March 30. Fruit of the Early Wonderful variety ripens several days earlier than that of the subject variety. It should be noted that the order of bloom and fruit ripening of the two varieties is reversed from the order of bud break and leaf development therein.

BRIEF DESCRIPTION OF THE DRAWING

The accompanying drawing is a color photograph of three typical whole fruits of the subject variety viewed at different angles, and a fruit halved to disclose the arils and partitions.

DETAILED DESCRIPTION

Referring more specifically to the pomological details of this new and distinct variety of pomegranate tree, the following has been observed under the ecological conditions prevailing at the designated orchard in Tulare County, Calif. All of the color code identifications are by reference to the Maerz and Paul Dictionary of Color, Second Edition, Published in 1950 by McGraw-Hill Book Company, Inc. except where common descriptive terms are employed.

TREE

Size: Normal for pomegranate 15 to 18 feet (4.5 m. to 5.5 m.).

Figure: Globular/bush.

Productivity: Good. Three to four No. 60 field boxes per tree at maturity.

Bearing: Not alternate, varies with cultural and weather conditions.

Trunks: Multiple, with scaly surface, usually grows to 8 in. (20 cm) diameter and 4 feet (120 cm) to heading out.

Branches:

*Size.*—To 1 in. (25 mm) diameter for fruiting wood, larger to scaffolds.

*Surface.*—Smooth.

*Color.*—Light green with tan ribs.

*Lenticels.*—Numerous, up to 25 per in. (1 per mm); small; circular when young, growing to over 1/16 in. (1.6 mm) in length.

Twigs: Color "Brown Sugar" (15 H 11).

Leaves:

*Size.*—Slightly smaller than "Wonderful" variety (unpatented).

*Length.*—2 in. (50 mm).

*Width.*—$\frac{1}{2}$ in. (12 mm).

*Shape.*—Long oval.

*Color.*—Upper surface, "Chrome Green, Deep" (24 H 12); lower surface "Parrot Green" (21 L 6).

*Marginal form.*—Smooth.

*Glandular characteristics.*—None on leaf or stem.

*Petiole.*—Length, short—less than $\frac{1}{8}$ in. (3 mm); thickness, 1/16 in. (1.6 mm).

*Stipules.*—Variable, commonly with two.

Flower buds:

*Size.*—Similar to Wonderful, $1\frac{1}{2}$ in. (38 mm) before opening.

*Shape.*—Slightly elongated.

*Surface.*—Smooth, waxy, red.

Flowers:

*Dates of bloom.*—Mid April to July 1.

*Size.*—To $2\frac{1}{2}$ (63 mm) diameter.

*Color.*—Red with very slight orange cast.

*Pistil.*—Single.

*Stamens.*—40 or more.

Resistance to disease and insects: Similar to Wonderful variety. Less susceptible to attack by the omniferous leaf roller than many varieties. In this respect almost as resistant as the Wonderful variety.

FRUIT

Maturity: Sept. 12 in 1979, 7 to 10 days before Wonderful variety.

Size:

*Uniformity.*—Varies directly with time of bloom, earliest bloom gives largest fruit.

*Diameter.*—$3\frac{1}{2}$ in. (90 mm).

*Axial length.*—$3\frac{1}{4}$ in. (83 mm).

Form: Typical pomegranate form with prominent crown of calyx segments at apex; symmetrical base slightly flattened near stem attachment.

Stem: Very short, less than $\frac{1}{4}$ in. (6 mm); caliper to $\frac{1}{4}$ in. (6 mm).

Rind:

*Texture.*—Hard surface, slightly corky and tough.

*Tendency to crack.*—Similar to Wonderful variety; crack after winter rains commence.

*Exterior color.*—Background ranging from "Candy Pink" (2 H 10) to "Afghan" (5 L 6) with the lighter portions of the background having spots of "Afghan".

*Partition color.*—"Maise" (10 G 5).

Aril:

*Color.*—"Oxheart" (6 L 5) through "Cherry Blossom" (4 J 4) to clear.

*Juice.*—Typical pomegranate flavor, sweet by September 1.

*Aroma.* —Slight, typical pomegranate (grenadine).

*Acidity.*—1.85 percent when ripe.

*Eating quality.*—Good flavor and juice content, pleasant acidity with sugar and distinctive grenadine flavor.

Use: Fresh fruit market and juice extraction.

Although the new variety of pomegranate tree possesses the described characteristics as a result of the growing conditions prevailing in Tulare County, Calif., in the San Joaquin Valley, it is to be understood that variations of the usual magnitude in characteristics incident to growing conditions are to be expected.

Having thus described and illustrated my new variety of pomegranate tree, what is claimed as new and desired to be secured by Letters Patent is:

1. A new and distinct variety of pomegranate tree, substantially as illustrated and described, characterized particularly as to novelty by its bearing of fruit which has a deeper red color of its rind and arils and which ripens from seven to ten days earlier than fruit of the "Wonderful" (unpatented) variety of pomegranate tree, which matures four to seven days later than the fruit of the Early Wonderful pomegranate tree (U.S. Plant Pat. No. 3,520) from which it is further distinguished by blooming from mid April to July 1st as contrasted with a blooming period commencing March 22 and reaching full bloom by March 30 for the Early Wonderful and by smaller leaves than the Early Wonderful and which new variety has a substantially higher acid content than fruit of the Granada variety of pomegranate tree (U.S. Plant Pat. No. 2,618) or the Early Red variety (U.S. Plant Pat. No. 2,723) which varieties the fruit of the subject variety most nearly resembles in appearance.

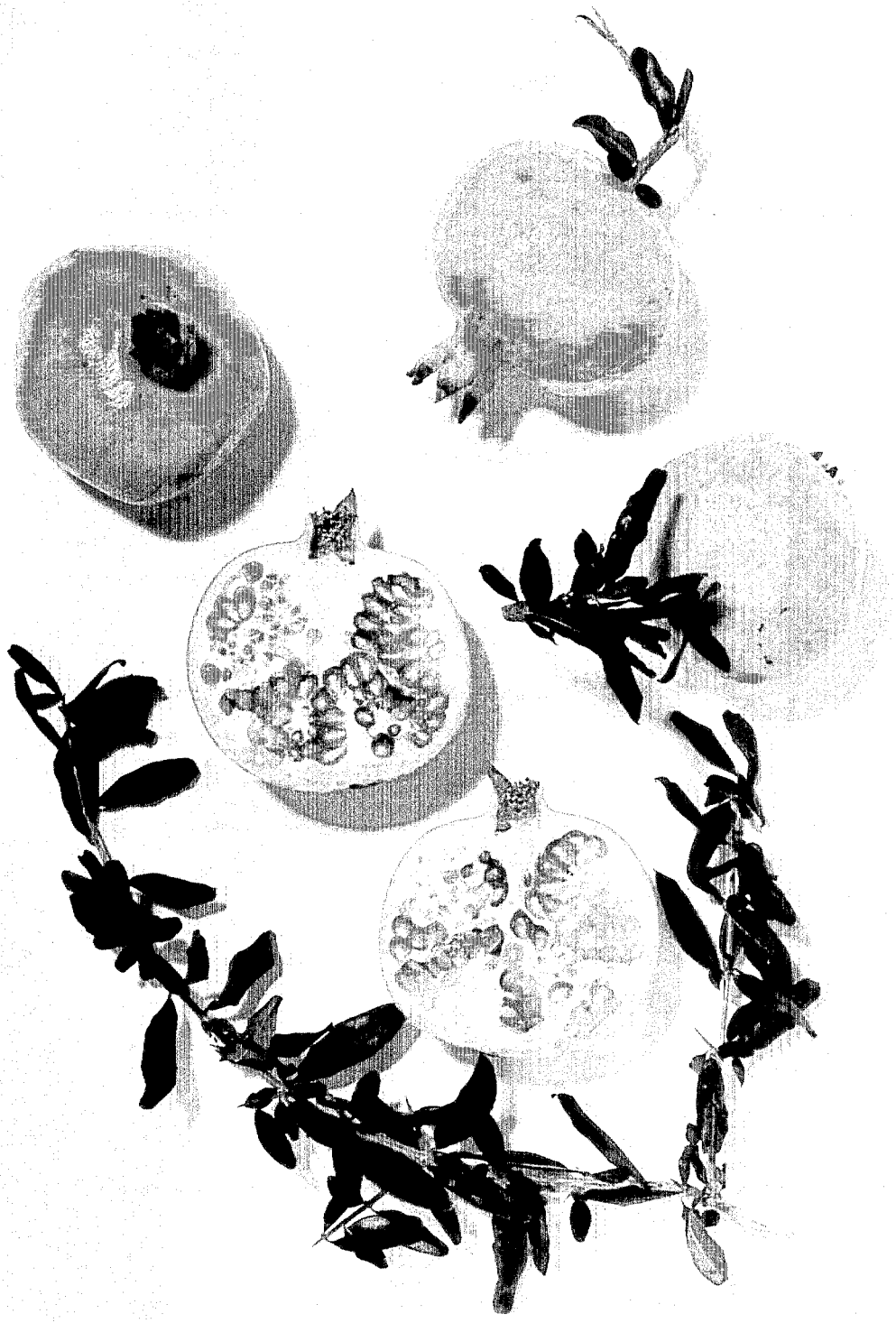

* * * * *